United States Patent [19]

Bates

[11] 4,299,795
[45] Nov. 10, 1981

[54] SAMPLE TUBE

[76] Inventor: William T. D. Bates, 16 Middlemarch, Daventry, Northamptonshire, England

[21] Appl. No.: 171,951

[22] Filed: Jul. 24, 1980

[30] Foreign Application Priority Data

Jan. 7, 1980 [EP] European Pat. Off. ........ 80300063.7

[51] Int. Cl.³ .................. B01L 3/02; G01N 1/10
[52] U.S. Cl. .................. 73/864.01; 422/102; 422/100
[58] Field of Search .................. 73/425.4 R, 425.4 P, 73/425.6, 61.4; 141/130, 31; 422/100, 102; 137/533, 533.11; 128/163, 766

[56] References Cited

U.S. PATENT DOCUMENTS

| | | | |
|---|---|---|---|
| 2,692,751 | 10/1954 | Felver | 137/533.11 |
| 2,930,238 | 3/1960 | Kellett | 73/425.4 P |
| 3,734,079 | 5/1973 | Weber | 73/61.4 |
| 3,864,979 | 2/1975 | Ayres | 73/425.4 P |
| 3,891,392 | 6/1975 | Betts et al. | 73/425.4 P |

*Primary Examiner*—William F. Smith
*Assistant Examiner*—Chris Konkol
*Attorney, Agent, or Firm*—Scrivener, Clarke, Scrivener and Johnson

[57] ABSTRACT

A sample tube for obtaining a column of liquid of predetermined height in laboratory applications comprises a simple and effective construction, with a local restriction in internal diameter a predetermined distance from an inlet end and a movable valve member such as a lead shot disposed in the tube between the restriction and the opposite end, for co-operating with the restriction to retain a column of liquid at the level of the valve member and restriction by surface tension effects. In operation, liquid is drawn into the tube by suction to a level substantially above restriction, then the suction is removed and the liquid is allowed to drain out of the end, passing the lead shot owing to an imperfect seal between the lead shot and the restriction. When the liquid reaches the level of the lead shot and restriction, it is retained at this level by surface tension effects interacting with the lead shot and restriction.

5 Claims, 1 Drawing Figure

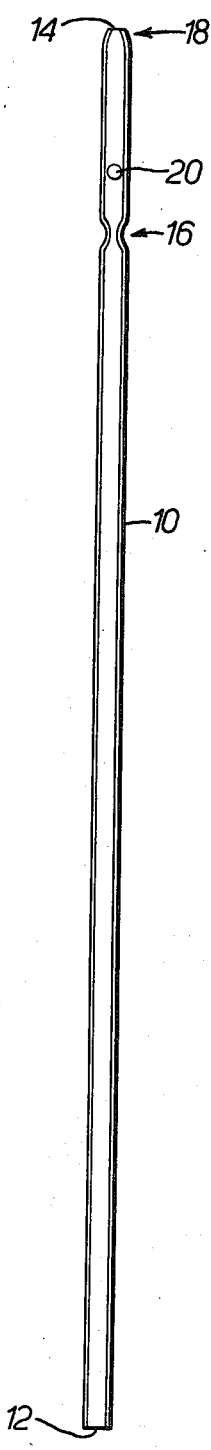

SAMPLE TUBE

This invention relates to a sample tube for obtaining a column of liquid of predetermined length in laboratory applications, particularly when carrying out sedimentation tests.

It is known in laboratory testing to obtain a column of liquid by suction to the upper end of a tube dipped at its lower end in the liquid sample. It is known for a plug of fibrous material to be placed in the tube before sampling at the required length from the lower end of the tube, the liquid being sucked into the tube to a level above the plug and then allowed to flow out until the plug, by surface tension effects, holds the liquid to the level of the plug. A particular test is then to allow sediments in the liquid to settle in time and this test is applicable to blood analysis.

However, the insertion of plugs into tubes is difficult to automate and tends to require a manual exercise.

This invention provides a sample tube having an inlet end for liquid to be sampled and an opposite end for application of suction, the tube being formed with a restriction locally in internal diameter a predetermined distance from the inlet end of the tube and a movable valve member being disposed in the tube between the restriction and said opposite end of the tube for co-operating with the restriction to retain a column of liquid at the level of the valve member by surface tension effects. Preferably the valve member is a spherical member, conveniently a lead shot, and the tube exhibits a further local restriction between the first restriction and said opposite end of the tube, or at said opposite end of the tube, to prevent the lead shot escaping.

An embodiment of this invention will now be described, by way of example only, with reference to the accompanying drawing, the single FIGURE of which shows a sample tube in accordance with the invention.

The sample tube shown comprises a straight glass tube 10 having opposite open ends 12,14 and having constant internal and external diameters along its length, except at restrictions 16 and 18. A valve member 20, in the form of a lead shot, is disposed in the tube between restrictions 16 and 18 and has a greater diameter than the internal diameter of the tube at restrictions 16 and 18 so as to be retained between them. However, the lead shot 20 has a smaller diameter than the internal diameter of the unrestricted tube, so as to be free to move along the tube. The restriction 18 is at the open end 14 of the tube but in general need be at any position between restriction 16 and end 14 whilst enabling some longitudinal movement of the lead shot 20. The restriction 16 is spaced from the end 12 of the tube by a distance equal to the required height of the column of liquid and in the example shown is substantially closer to the end 14.

In use, the end 12 of the tube is dipped into the sample liquid to be tested and suction is applied to the upper end 14 to draw the liquid into the tube. The lead shot unseats readily from the restriction 16 to enable the liquid to be drawn in freely. The suction is removed when the liquid level is above the restriction 16 and the lead shot seats on this restriction under its own weight. Then the liquid is allowed to drain, passing the lead shot owing to an imperfect sealing between the lead shot and restriction 16, until the liquid level reaches the level of the lead shot and restriction 16. At this level, the liquid is retained by surface tension effects, interacting with the lead shot and restriction 16.

The column of liquid thus obtained will be held indefinitely by these surface tension effects. For a sedimentation test, as when testing blood, the manner and extent to which settling occurs can then be monitored.

The sample tube which has been described is relatively simple to manufacture automatically and is easy and effective in use.

I claim:

1. A sample tube having a transparent, substantially rigid body portion to enable viewing of a test conducted in said tube, said body portion having a first end which serves as an inlet for sample liquid and a second end to which suction can be applied to draw liquid into said first end, the tube being formed with a local restriction in internal diameter a predetermined distance from the inlet end of the tube, and a movable valve member disposed in the tube between said restriction and said opposite end of the tube for co-operating with the restriction, said valve member and said restriction being constructed and arranged that when said valve member is seated on the restriction an imperfect seal is formed between said valve member and said restriction, the space defined by said imperfect seal between said restriction and the valve member seated thereon being of a size to allow liquid, after being drawn into the tube to substantially above said restriction, to drain through said imperfect seal until the liquid level reaches the level of said valve member and said restriction and then retain the level of the liquid at said level by surface tension effects interacting with said space of said imperfect seal.

2. A sample tube as claimed in claim 1, in which the valve member is arranged to seat on the restriction under its own weight before the liquid drains down to said level, and such that the liquid drains through said space between the valve member and restriction after the valve member seats on the restriction and until the liquid has drained down to said level.

3. A sample tube as claimed in claim 1 or 2, in which the valve member is generally spherical in shape.

4. A sample tube as claimed in claim 3, in which the valve member comprises a lead shot.

5. A sample tube as claimed in claim 1 or 2, in which the tube is provided with a second local restriction in its internal diameter between the first restriction and said opposite end of the tube, or at said opposite end of the tube, to prevent the valve member escaping through said opposite end of the tube.

* * * * *